United States Patent [19]
Kawashima et al.

[11] Patent Number: 5,462,929
[45] Date of Patent: Oct. 31, 1995

[54] TREATMENT OF PSORIASIS BY ADMINISTRATION OF 4-CARBAMOYL-1-β-D-RIBOFURANOSYLIMIDSZOLIUM-5-OLEATE

[75] Inventors: Makoto Kawashima, Tokyo; Kazuhiro Nagano; Kazuyoshi Hori, both of Hori; Hiroaki Ishikawa, Kanagawa; Masataka Morishita, Shizuoka, all of Japan

[73] Assignee: Asahi Kasei Kogyo Kabushiki Kaisha, Osaka, Japan

[21] Appl. No.: 190,165

[22] PCT Filed: Aug. 3, 1992

[86] PCT No.: PCT/JP92/00985

§ 371 Date: Apr. 11, 1994

§ 102(e) Date: Apr. 11, 1994

[87] PCT Pub. No.: WO93/02683

PCT Pub. Date: Feb. 18, 1993

[30] Foreign Application Priority Data

Aug. 6, 1991 [JP] Japan .................. 3-219301
Jul. 16, 1992 [JP] Japan .................. 4-212188

[51] Int. Cl.$^6$ .................................................. A61K 31/70
[52] U.S. Cl. ........................................ 514/43; 536/28.8
[58] Field of Search ............................ 514/43; 536/28.8

[56] References Cited

U.S. PATENT DOCUMENTS

| | | | |
|---|---|---|---|
| 3,888,843 | 6/1975 | Mizuno et al. | 536/43 |
| 4,788,061 | 11/1988 | Shore | 514/43 |
| 4,996,193 | 2/1991 | Hewitt et al. | 514/11 |
| 5,135,934 | 8/1992 | Behrens et al. | 514/297 |
| 5,204,329 | 4/1993 | Ackerman et al. | 514/15 |
| 5,283,257 | 2/1994 | Gregory et al. | 514/458 |

FOREIGN PATENT DOCUMENTS

| | | | |
|---|---|---|---|
| 50-121275 | 9/1975 | Japan | 536/28.8 |
| 57-156418 | 3/1981 | Japan | 514/43 |
| 0426626 | 1/1992 | Japan | 514/43 |
| 0421632 | 1/1992 | Japan | 514/43 |
| 9119498 | 12/1991 | WIPO | 514/307 |
| 9200739 | 1/1992 | WIPO | 514/307 |

OTHER PUBLICATIONS

Kamata et al., "Mechanism of the Immunosuppressive Action of Bredinin (Mizoribine)," *Saishin Igaku*, 41(11), 2509–2515 (1986); *Chem. Abst.*, 106(13), p. 3, Abstr. No. 95429r (1987); see original publication with english abstract included.

Holvey et al. eds., *Merck Manual of Diagnosis and Therapy*, 12th ed., Merck Research Laboratories, Rahway, N.J., 1972, pp. 1473–1475, particularly pp. 1474–1475.

Gennaro et al. eds., *Remington's Pharmaceutical Sciences*, 18th Ed., Mack Publishing Co., Easton, Pa., 1990, Chapter 61 (Immunoactive Drugs), see pp. 1142–1143.

Kamata et al., "Mechanism of the Immunosuppressive Action of Bredinin (Mizoribine)," *Saishin Igaku*, 41(11), 2509–2515 (1986); *Chem. Abstr.*, 106(13), p. 3, Abstr. No. 95429r (1987); only Abstract supplied.

Kobayashi et al., "Therapeutic Effect of Mizorubine on Spontaneous Autoimmune Disorders in MRL/Mp-Ipr/Ipr Mice," *Ensho*, 12(2), 193–197 (1992); *Chem. Abstr.*, 117(5), p. 46, Abstr. No. 40028f (1992); only Abstract supplied.

Berkow et al. eds., *Merck Manual of Diagnosis and Therapy*, 16th Ed., Merck Research Laboratories, Rahway, N.J., 1992, pp. 2435–2436.

Primary Examiner—Douglas W. Robinson
Assistant Examiner—L. Eric Crane
Attorney, Agent, or Firm—Young & Thompson

[57] ABSTRACT

A composition for curing proliferative skin diseases containing 4-carbamoyl-1-β-D-ribofuranosyl-imidazolium 5-olate (mizoribine) as an active ingredient. It has a potent activity of inhibiting the growth of keratinocytes and an improved effect of curing psoriasis, so that it is useful for curing proliferative skin diseases. Further it has only an extremely reduced toxicity, is highly safe, and can be administered for long and perorally.

2 Claims, 5 Drawing Sheets

200 μm
CONTROL
(0 μg/ml)

CULTURED DAY 5TH

FIG. 7

CULTURED DAY 7TH

FIG. 8

CULTURED DAY 9TH

TREATMENT OF PSORIASIS BY ADMINISTRATION OF 4-CARBAMOYL-1-β-D-RIBOFURANOSYLIMIDSZOLIUM-5-OLEATE

FIELD OF THE INVENTION

The present invention relates to a composition for curing proliferative skin diseases containing 4-carbamoyl-1-β-D-ribofuranosyl-imidazolium-5-olate as an active ingredient.

PRIOR ARTS 4-carbamoyl-1-β-D-ribofuranosyl-imidazolium-5-olate is a nucleic acid related compound which was found in a cultured broth of the strain *Eupenicillium brefeldianum* M-2199 belonging to genus Streptomyces and is given a generic name mizoribine. It is easily soluble in water and is a weakly acidic substance which is brown and decomposes with foaming at approximately 200° C. Various production processes of mizoribine have been known. [*J. Antibiotics*, 27(10); 775 (1974), *Chem. Pharm. Bull.*, 23; 245 (1975), Japanese Patent Unexamined Publication No. 48-56849, ibid., No. 51-1693, ibid., No. 50-121275, ibid., No. 50-121276 and others]

4-carbamoyl-1-β-D-ribofuranosyl-imidazolium-5-olate (hereinafter sometimes designated as mizoribine) has an immunosuppressive activity and suppresses the rejection of the transplantation of an organ such as kidney. Mizoribine anhydrate crystal (bredinin. trade mark, tablet. Toyo Jozo Co.) has been applied as an immunosuppressant, which is prescribed for oral administration, with initial dose 2–3 mg/kg/day and maintenance dose 1–2mg/kg/day.

PROBLEMS TO BE SOLVED BY THE INVENTION

A proliferative skin disease, especially psoriasis is a common chronic, squamous dermatosis, marked by exacerbations and remissions. It is characterized clinically by the presence of rounded, circumscribed, erythemtous, dry, scaling patches of various sizes, covered by grayish white or silvery white, umbilicated and lamellar scales. Central clearing and coalescence of the lesions produce a wide variety of clinical configurations, including annular or circinate, discoid or nummular, figurate, and gyrate arrangements. The most distinctive histological findings in well-developed psoriasis are characterized by proliferative and hypertrophic epidermis, disappearance of granular layer and promotion of parakeratosis, and migrating the leukocytes into epidermis and horny layer from edematous and elongated derml papilla, and resulted to form Munro microabscesses.

Observing the total lesions of psoriasis beginning from primary puncrate lesion to well-developed sheet lesion, typical histopathological findings are observed in a central part at initial stage, thereafter, with developing an efflorescence, only found to move in peripheral region. Generally infiltration of mononuclear cells in an upper layer of dermis and nonspecific dermatitis which show proliferation and hypertrophy of epidermis with thick granular layer, are observed.

Epidermis of non-lesional skin of psoriasis patients responds easily proliferative reaction with stimulation as compared with that of the normal persons. Namely, the proliferative nature on epidermis is found, followed by nonspecific dermatitis caused by external or internal stimulation.

Therapeutics and treatment methods are disclosed, for example, in Japanese Patent Unexamined Publication No. 52-15827, ibid., No. 52-15828, ibid., No. 55-66511 and ibid., No. 53-47536. Among these, the former three publications relate to a medicine for external application and a medicine for topical injection, and the latter one discloses medicament for oral administration. These medicaments have been shown to have insufficient therapeutic efficacy and were not of practical use. Further no toxicological data was shown in the last one even though it is an oral medicament.

Cyclosporin which is known as an immunosuppressant is applied to a psoriasis patient (for example, refer to *New England J. Med.*, 1989; 301: 555. Lancet, 1984; 11: 981–2, ibid., 1985; 1: 335. *J. Am. Med. Assoc.*, 1986; 256: 3110–6, *Brit. Med. J.*, 1986; 293:731–2 and *Brit. J. Dermtol.*, 1986; 114: 615–20).

Inhibition of growth of epidermal keratinocyte cells is thought to be an effective treatment for psoriasis. Inhibitory action on growth of cultured human epidermal keratinocyte cells by cyclosporin has been reported (for example refer to *Brit. J. Dermatol.*, 1990; 122: 173–180).

Long term administration of cyclosporin causes renal lesion, and it can not be administered for long term Moreover when the medication by cyclosporin is discontinued, recurrence of proliferative dermatological disease such as psoriasis has been reported (for example, refer to "The Society for Investigational Dermatology. 1991, May 1–3, Annual Meeting").

MEANS FOR SOLVING THE PROBLEMS

The inventors of the present invention have studied to discover a medicament for curing proliferative skin diseases having low toxicity, higher safety value, administrable for long terms, for oral administration and higher applicability.

An object of the present invention is to provide a composition for curing proliferative skin diseases containing 4-carbamoyl-1-β-D-ribofuranosyl-imida-zolium- 5-olate as an active ingredient.

The proliferative skin disease, for which the composition of the present invention is applied, is not limited and is, for example, psoriasis, atopic dermatitis, nonspecific dermatitis, allergic contact dermatitis, primary irritant contact dermatitis, cutaneous basal cell carcinoma, cutaneous planocellular carcinoma, wart, lameliar ichthyosis, epidemolytic keratosis, solar induced precancerous keratosis, benign keratosis, ache, seborrheic dermatitis, atopic dermatitis of bleeding animals and scabies. Preferably the composition is effective for treatment of psoriasis.

Mizoribine is as previously described, a commercially available immunosuppressive agent. Its toxicity is as follows. Acute toxicity ($LD_{50}$); mice, male, p.o.: >4883mg/kg, s.c.: >4883 mg/kg, i.v.: >3042 mg/kg, i.m.: >2800 mg/kg, female, p.o.: >4883 mg/kg, s.c.: >4883 mg/kg, i.v.: >3042 mg/kg, i.m.: >2800 mg/kg; rats, male, p.o.: >3100 mg/kg, s.c.: >4161 mg/kg, i.v.: >2572 mg/kg, i.m.: >2800 mg/kg; female, p.o.: >2847 mg/kg, s.c.: >3975 mg/kg, i.v.: >2606 mg/kg, i.m.: >2800 mg/kg. It has low toxicity and is safe as a medicament. In addition, mizoribine has shown no nephrotoxicity, lower blood accumulation residue and less transfer into brain. [refer to, for example, *Applied Pharmacol.*, (1978) 15C5); 829–835].

In the present invention, commercially available mizoribine preparation for oral administration (Trade name: Bredinin Tablet) can preferably be used. Further, conventional formulations such as capsules, granules for oral administration, suppositories, percutaneous absorption preparation and injections can be prepared.

An amount for administration of mizoribine in the present invention is, for example, 1–10 mg/kg body weight/day in adult, 1–3 times in a day. Preferably, mizoribine preparation for oral administration, 25 mg or 50 mg tablet is prescribed for adult patient, body weight 50–60 kg, 100–300 mg of mizoribine in one administration for twice or thrice in a day. The composition of the present invention can be administered for long terms without adverse effect because it contains as a main effective ingredient mizoribine of low toxicity.

Following examples illustrate the present invention but are not construed as limiting.

EXAMPLE 1

Growth inhibition activity of mizoribine on cultured human epidermal keratinocyte cells was examined in order to prove the efficacy of mizoribine as a medicament for curing proliferative skin disease such as psoriasis.

I. Materials:

Epi Pack kit (Sanko Pure Chemicals Co.):
  Normal human epidermal keratinocyte cells
  (NHEK: human penile prepuce originated secondary cultured cells)
  Epidermal keratinocyte cell growth medium (K-GM)
  HEPES buffer saline solution
  Trypsin/EDTA solution
  Neutralization solution for trypsin
Mizoribine (Toyo Jozo Co.)
24-well culture plate (2 cm$^2$/well)

II. Methods:

(1) NHEK was subcultured according to the instruction described in the manual for Epi Pack, to obtain tertiary subcultured cells. Epi Pack medium on arrival was exchanged by fresh K-C,M to which added attached bovine pituitary gland extract (BPE), then NHEK was cultured at 37° C. and on the first day, tertiary cultivation was performed under the same conditions.

(2) Mizoribine arthydrate was dissolved to prepare 250 µg/ml solution in K-GM, subjected to sterilization by filtration and diluted 5-fold steps with K-GM, then the mizoribine solution was added in NHEK. The pH of each solution is shown in Table 1.

TABLE 1

| Mizoribine concentration (µg/ml) | 0 | 0.16 | 0.8 | 4 | 20 | 100 | 500 | 2500 |
|---|---|---|---|---|---|---|---|---|
| pH | 7.4 | 7.4 | 7.4 | 7.4 | 7.4 | 7.4 | 7.4 | 7.2 |

(3) Mizoribine addition was performed by the following schedule.

On the day of starting initial cultivation:
NHEK, 2500 cells/cm$^2$ (5000 cell/well), was inoculated in six 24-well culture plates.

Cultured, day 1: exchange medium and mizoribine addition (amount added: 0, 0.16, 0.8. 4, 20, 100, 500 and 2500 µg/ml)

Cultured, day 3: exchange medium and mizoribine addition (amount added: the same as above)

Cultured, day 5, day 7 and day 9: Photographs were taken on the central part of the two plates of 24-well culture plate, and calculated the number of cells.

On the remaining other plates, the medium was exchanged and mizoribine was added. (amount added: the same as above)

(4) Arrangement for addition of mizoribine was set up as shown in Table 2.

TABLE 2

|   | 1 | 2 | 3 | 4 | 5 | 6 |
|---|---|---|---|---|---|---|
| A |   | 0 |   |   | 20 |   |
| B |   | 0.16 |   |   | 100 |   |
| C |   | 0.8 |   |   | 500 |   |
| D |   | 4 |   |   | 2500 |   |

(Numerals in the table indicate an amount of mizoribine added µg/ml, n=3)

Result, indicated with number of cells measured by Coulter counter on the cultivation, day 5, is shown in Table 3.

TABLE 3

| Mizoribine concentration (µg/ml) | Number of cells/cm$^2$ (×10$^3$) | Inhibition rate* (%) |
|---|---|---|
| 0 (control) | 95.5 | — |
| 0.8 | 69.7 | 27 |
| 4 | 8.6 | 91 |
| 20 | 4.5 | 95 |

*inhibition rate (%) = 95.5 × 10$^3$ − A95.5 × 10$^3$ × 100 wherein A: number of cells/cm$^2$ on mizoribine added group.

(5) Method of calculating number of cells

On the cultivation, day 5, day 7 and day 9, respectively, one plate of 24-well culture plate was applied for calculating number of cells by Coulter counter, and the other one plate was applied for dye uptake method.

(a) Measurement by Coulter counter
   Each well: washed with 0.2 ml of HEPES buffer saline solution
   ↓
   add 0.2 ml of trypsin/EDTA solution,
   allow to stand at room temperature for 10 minutes,
   then tap the 24-well culture plate by solid face to remove the cells.
   ↓
   added 0.3 ml of trypsin neutralization solution and separated the cells by pipetting.
   ↓
   calculation of cells by Coulter counter
   (counted particles over 7 μm φ)

(b) Dye uptake method
   After removing the medium in each well, add 2.5% glutaraldehyde/PBS 0.5 ml, fix, wash and dry.
   ↓
   staining with 0.05% methylene blue solution, washing and drying.
   ↓
   extraction of pigment with 0.1 N HCl,
   measured $OD_{665\,nm}$ using multiphotometer for 96-well culture plate.
   Control group without addition of mizoribine is indicated as 100%.

III. Results and Discussion (1) Growth appearance of control group (no addition of mizoribine):

Cultivation, day 5: many spherical cells which seem to be under cell division were observed.

Cultivation, day 7: slightly over confluent.

Cultivation, day 9: over confluent, cells being under exfoliated.

(2) On mizoribine addition over 20 μg/ml, number of cells are approximately $4 \times 10^3$ cells/ml with constant level. This might be a result of termination of cell growth after growing the cells, whose initial concentration was $2.5 \times 10^3$ cells/ml, without presence of mizoribine in one day.

(3) On mizoribine addition at 4 μg/ml, significant growth inhibition was observed and cells were grown extremely slowly.

(4) On mizoribine addition at 8 μg/ml, significant growth inhibition was observed.

Figure 1:
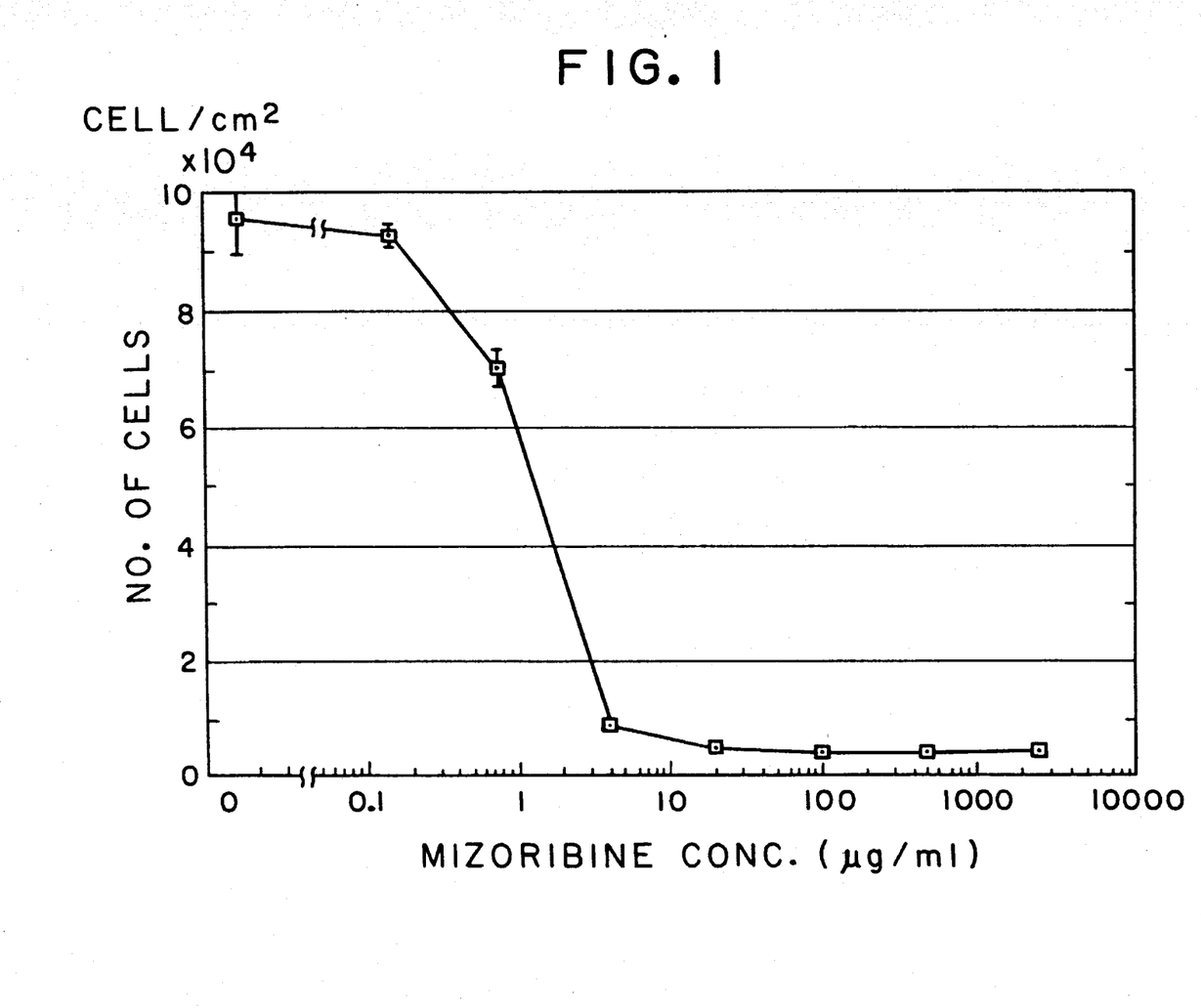
FIG. 1: A graph showing a relation of number of cells and mizoribine concentration (Coulter counter method)
Figure 2:
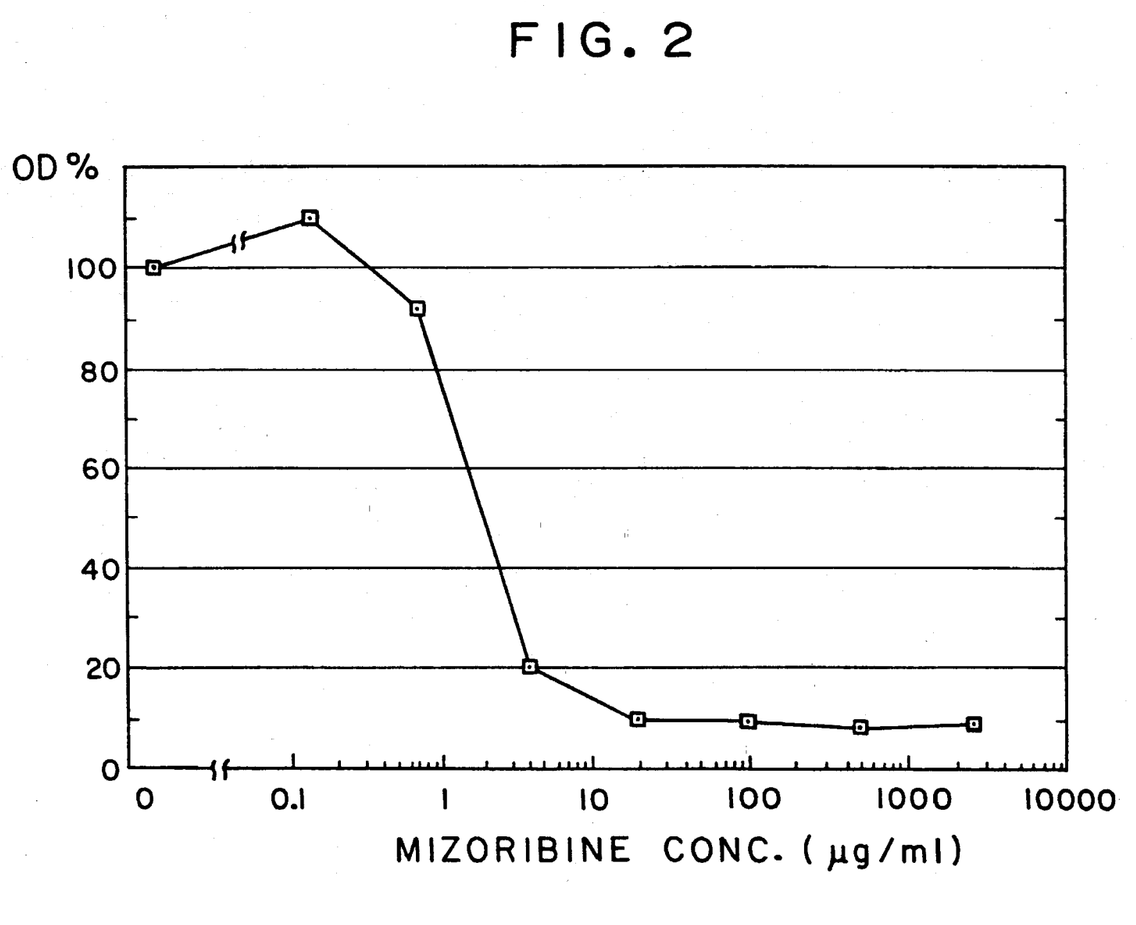
FIG. 2: A graph showing a relation of number of cells and mizoribine concentration (Dye uptake method)

(5) A graph showing the relations between number of cells and concentration of mizoribine on the cultivation day 5 by Coulter counter is shown in FIG. 1. Also in FIG. 2, the result by dye uptake method is shown.

(6) On the dye uptake method, slightly lower growth inhibition rate with mizoribine addition was observed as compared with that of Coulter counter method. Significant increase in the value at $OD_{665}$ on the dye uptake method was observed even though no difference in the number of cells was found as compared with the control value on the Coulter counter method. This phenomenon my be a result of increased dye uptake in a cell by an action of mizoribine on the cell morphology from lower level of its concentration.

Figure 3:
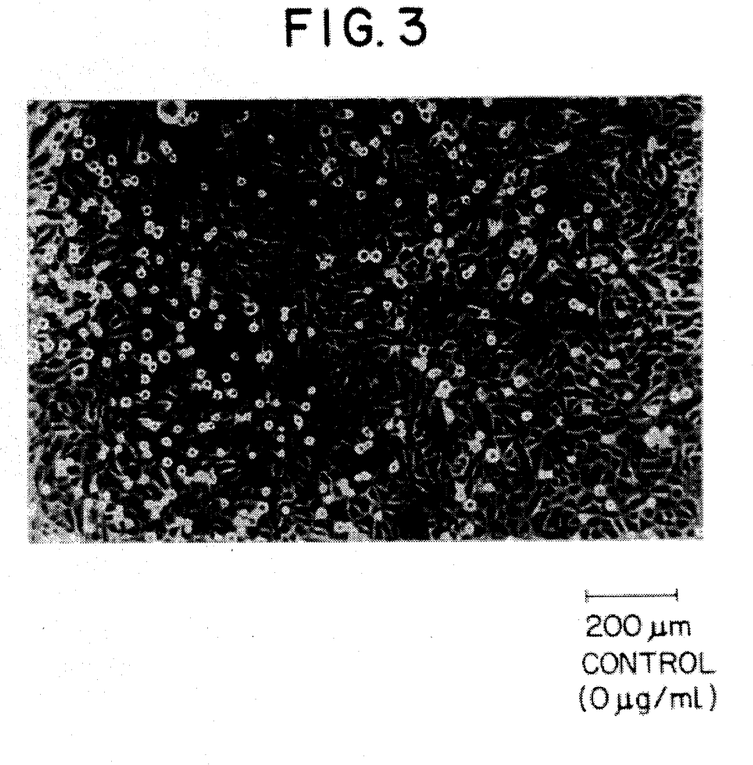
FIG. 3: Photographs showing microscopical observation of cells cultured with mizoribine concentration at 0 µg/ml (control) on day 5 (magnification: × 76.5)
Figure 4:
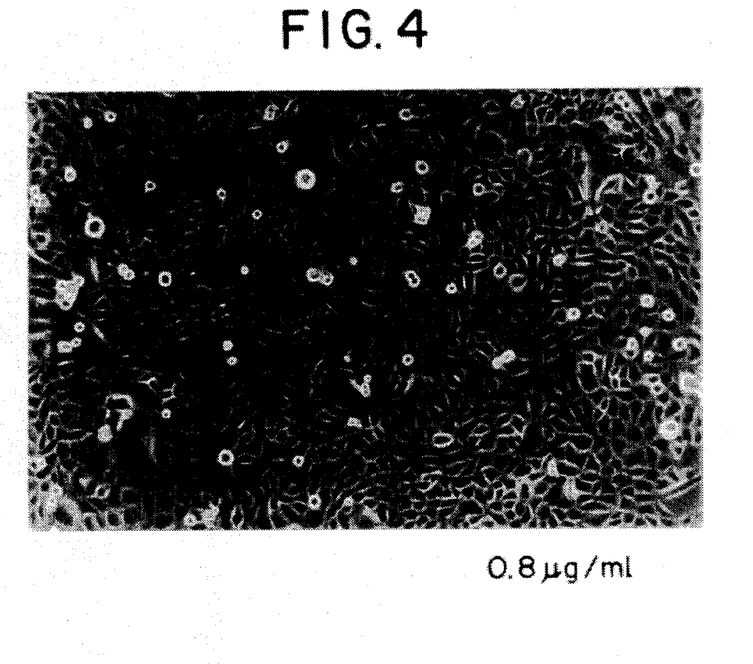
FIG. 4: Photographs showing microscopical observation of cells cultured with mizoribine concentration at 0.8 µg/ml on day 5 (magnification: ×76.5)
Figure 5:
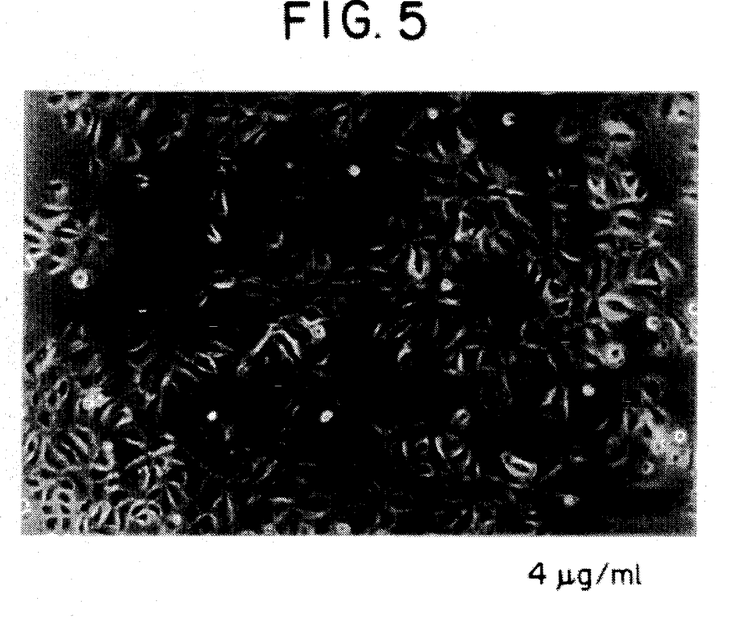
FIG. 5: Photographs showing microscopical observation of cells cultured with mizoribine concentration at 4 µg/ml on day 5 (magnification: ×76.5)
Figure 6:
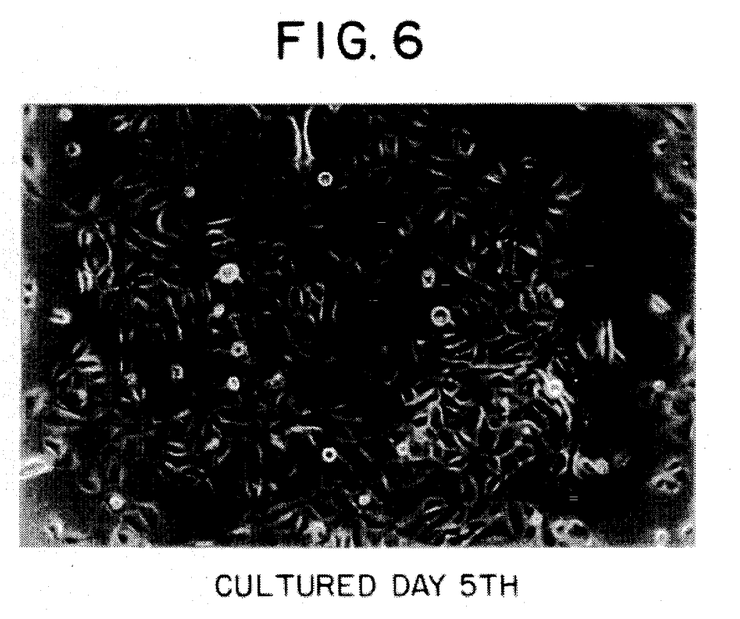
FIG. 6: Photographs showing microscopical observation of cells cultured with mizoribine concentration at 4 µg/ml on day 5 (magnification: ×76.5)
Figure 7:
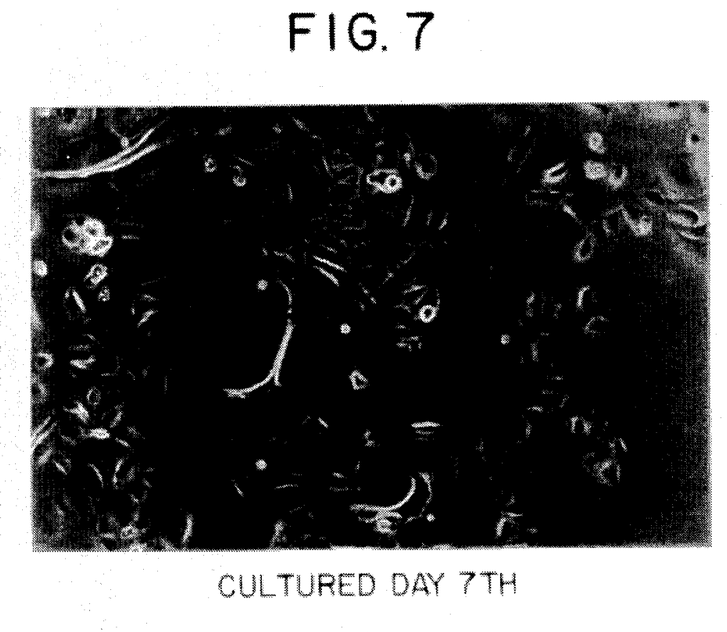
FIG. 7: Photographs showing microscopical observation of cells cultured with mizoribine concentration at 4 µg/ml on day 7 (magnification: ×76.5)
Figure 8:
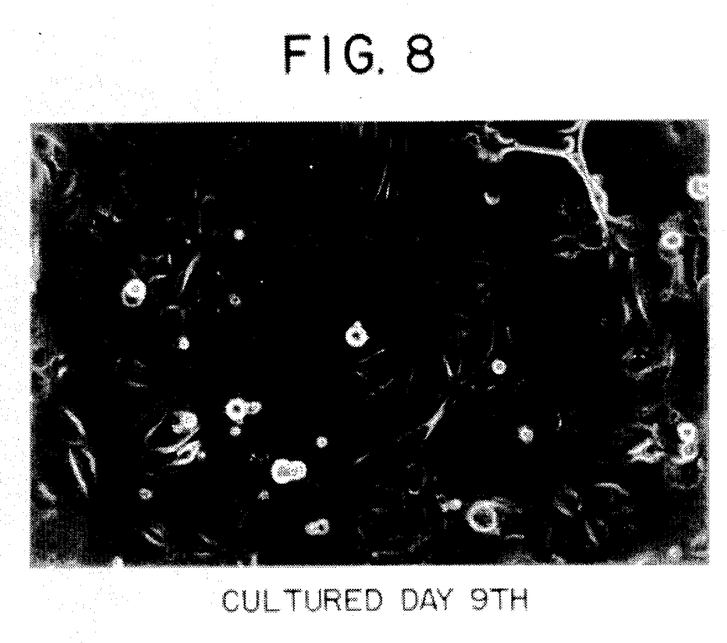
FIG. 8: Photographs showing microscopical observation of cells cultured with mizoribine concentration at 4 µg/ml on day 9 (magnification: ×76.5)

(7) In FIG. 3–FIG. 5, photographs of microscopical observation of cells on the cultivation day 5, in which mizoribine was added at the concentration of 0, 0.8 and 4 μg/ml, are shown. Also, in FIG. 6–FIG. 8, photographs of microscopical observation of cells on the cultivation day 5, day 7 and day 9, in which mizoribine was added at the concentration of 4 μg/ml, are shown. Magnification of microscopic photographs is ×76.5 in each case. A morphology of cells which being changed widely expanded shape by an addition of mizoribine was observed.

Blood level of mizoribine at clinical trials was reported to be approximately 1 μg/ml [Transplantation, 17 (supplement): 585 (1982)]. Dermal level of mizoribine in rat is almost equal in plasma level. Accordingly mizoribine has been shown to be effective for significant inhibition of growth of human epidermal keratinocyte cells at the concentration which is presumed to reach the level in the clinical use.

EXAMPLE 3

1. Object: Effect of mizoribine on the treatment of psoriasis.

2. Subject: Patients of psoriasis.

(1) Psoriasis vulgaris with median grade which satisfied within the following standard.

a) No consideration for the distinction of sex, inpatient and outpatient.

b) aged over 15 and below 70.

c) PASI [Psoriasis area and Severity Index; *Darmtologica*, 157; 238–244, 1978: Table 4] over 20 at initial stage of the test.

(2) Following patients are omitted.

a) within 2 weeks prior to start mizoribine administration, a person who had been treated with steroid external preparation over the very strong, steroid preparation (peroral preparation), methotrexate, other immunosuppresant, etretinate or PUVA.

b) patients who have suffered with severe bacterial, viral or mycotic infection.

c) person with complication or anamesis of malignant tumor.

d) person with cardiac disorder, renal disorder, blood disorder, gastrointestinal bleeding, peptic ulcer, and other serious complication, and anamesis.

e) a woman in pregnancy or in a lactation, and who suspects being pregnant.

f) in addition, persons who are determined by the doctors-in-charge as unfit to participate.

3. Clinical trials (1) Medicament: Preparation containing mizoribine 50 mg in a tablet is used.

(2) Methods:

1) Dosage regimen:
   Mizoribine 300 mg/day, divided in 3 times, is administered after meal.

2) Term for dosage: 6 weeks

3) Prohibited other concomitant drugs.
   Concomitant use of the following preparation and others are prohibited.

a) Oral dosage of methotrexate, other immunosuppressant, etretinate and steroid preparations.

b) Ultraviolet treatment.

c) Other medicament which seem to be effective for psoriasis [Chinese indigenous medicine (Kampo-Yaku), anti-allergic drug, etc.]

4. Observations:
Clinical findings:
Following items were observed at the initial day of treatment and after 6 weeks, then results were recorded in a check sheet.
PASI:
1) Scoring method of dermal observation is shown in Table 4.

TABLE 4

| Score | 0 | 1 | 2 | 3 | 4 | 5 | 6 |
|---|---|---|---|---|---|---|---|
| erythema infiltration scaling | none | light | medium | high | extremely high | — | — |
| Psoriasis area | 0 | <10 | 10 < 30 | 30 < 50 | 50 < 70 | 70 < 90 | 90 < 100 |

2) Calculation method of PASI:

PASI=0.1 (Eh+Ih+Dh)×Ah+0.3 (Et+It+Dt)×At+ 0.2 (Eu+Iu+Du)×Au+0.4 (El+Il+Dl)×Al wherein Eh: a score in severity index of erythema in the head,
Ih: a score in severity index of infiltration in the head,
Dh: a score in severity index of scaling in the head,
Ah: a score in psoriasis area in the head,
Et: a score in severity index of erythema in the body,
It: a score in severity index of infiltration in the body,
Dr: a score in severity index of scaling in the body,
At: a score in psoriasis area in the body,
Eu: a score in severity index of erythema in the upper limbs,
Iu: a score in severity index of infiltration in the upper limbs,
Du: a score in severity index of scaling in the upper limbs,
Au: a score in psoriasis area in the upper limbs,
El: a score in severity index of erythema in the lower limbs.
Il: a score in severity index of infiltration in the lower limbs,
Dl: a score in severity index of scaling in the lower limbs,
Al: a score in psoriasis area in the lower limbs.

3) Example of score calculation:

A patient whose symptoms of psoriasis are;

in the head: the degree of erythema: medium
  the degree of infiltration: high
  the degree of scaling: medium
  the area of psoriasis lesion: 40% of the head in the body: the degree of erythema: high
  the degree of infiltration: high
  the degree of scaling: high
  the area of psoriasis lesion: 35% of the body in the upper limbs: the degree of erythema: fairly high
  the degree of infiltration: extremely high
  the degree of scaling: extremely high
  the area of psoriasis lesion: 75% of the upper limbs in the lower limbs: the degree of erythem: high
  the degree of infiltration: medium
  the degree of scaling: medium
  the area of psoriasis lesion: 80% of the lower limbs The degree of score can be calculated as follows:

|  | Erythema | Infiltration | Scaling | Psoriasis area |
|---|---|---|---|---|
| Head | 3 | 3 | 2 | 3 |
| Body | 3 | 4 | 3 | 3 |
| Upper limbs | 4 | 4 | 4 | 4 |
| Lower limbs | 3 | 2 | 2 | 4 |

PASI = 0.1 × (3 + 3 + 2) × 3 + 0.3 × (3 + 4 + 3) × 3 + 0.2 × (4 + 4 + 4) × 4 + 0.4 × (3 + 2 + 2) × 4 = 35.4

4) Adverse effect:

During the period of administration of the drug, accompanied symptoms, which have newly appeared and were thought to be closely related to and can not be denied with the relation for the administered medicament, are checked and searched in details of the fact, the day appeared, the day disappeared, degree, treatment, result and relation with the test drug, and studied the presence of adverse effect.

5) Items on evaluation:

On the treatment of administration of the drug after 6 weeks, the results were evaluated.

(1) Overall improvement:

Considering the progress of PASI, following five degrees of evaluation were applied as compared with the condition before administration.

1. significantly improved,
2. improved,
3. slightly improved,
4. no change,
5. exacerbation (2) Usefulness:

Considering the overall improvement and safety evaluation such as adverse effect, following five degrees of evaluation were applied.

1. extremely useful,
2. useful,
3. slightly useful,
4. useless,
5. worse

6) Result and discussion:

Evaluation: PASI shown in Table 4, was used.

In Table 5, curing effect of mizoribine on the treatment of psoriasis is shown.

TABLE 5

| No. | Name | Age | Sex | Term for psoriasis (year) | PASI pre | PASI post | Adverse effect |
|---|---|---|---|---|---|---|---|
| 1 | S.K. | 41 | M | 10 | 20 | 12 | None |
| 2 | Y.N. | 23 | M | 5 | 41.4 | 20 | None |
| 3 | T.A. | 42 | M | 21 | 24.3 | 14 | None |
| 4 | Y.S. | 29 | M | 7 | 21 | 12 | None |

According to the effect shown in Table 5, an overall improvement rate was considered to be 2 and usefulness was considered to be 2.

EFFECT OF THE INVENTION

As explained hereinbove, a composition for curing proliferative skin diseases of the present invention has strong inhibitory action on the growth of epidermal keratinocyte cells as a psoriasis model, and also provides an improvement in the curative effect for psoriasis patients. The medicament composition of the present invention is useful for treatment of proliferative skin disease. Further it has higher safety, and can be administered for long term and perorally.

We claim:

1. A method of treating psoriasis which comprises administering to a patient afflicted with psoriasis an amount of 4-carbamoyl-1-β-D-ribofuranosyl-imidazolium-5-olate, said amount being effective to ameliorate symptoms of psoriasis.

2. The method according to claim 1, wherein said effective amount is administered orally and ranges from 1 to 10 mg/kg per body weight of patient per day.

* * * * *

UNITED STATES PATENT AND TRADEMARK OFFICE
CERTIFICATE OF CORRECTION

PATENT NO. : 5,462,929
DATED : October 31, 1995
INVENTOR(S) : Makoto Kawashima, et al It is certified that error appears in the above-indentified patent and that said Letters Patent is hereby corrected as shown below:

On the title page item [54],

Correct the spelling of "RIBOFURANOSYLIMIDAZOLIUM".

On the title page, item [75], lines 2-3, change "both of Hori" to --both of Shizuoka--;

item [57], line 3, change "5-olate" to --5-oleate--.

In column 1, line 10, change "5-olate" to --5-oleate--;

line 14, change "5-olate" to --5-oleate--;

line 26, change "5-olate" to --5-oleate--.

UNITED STATES PATENT AND TRADEMARK OFFICE
CERTIFICATE OF CORRECTION

PATENT NO. : 5,462,929
DATED : October 31, 1995
INVENTOR(S) : Makoto Kawashima, et al It is certified that error appears in the above-indentified patent and that said Letters Patent is hereby corrected as shown below:

In column 2, line 39, change "5-olate" to --5-oleate--.

In column 9, claim 1, line 7, change "5-olate" to --5-oleate--.

Signed and Sealed this

Fifteenth Day of October, 1996

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,462,929
DATED : October 31, 1995
INVENTOR(S) : Kawashima, et al

It is certified that error appears in the above-identified patent and that said Letters Patent is hereby corrected as shown below:

On the title page, item [54] and column 1, in the title "OLEATE" should read --- OLATE --.

Signed and Sealed this

Twenty-sixth Day of November 1996

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,462,929
DATED : October 31, 1995
INVENTOR(S) : Kawashima, et al

It is certified that error appears in the above-identified patent and that said Letters Patent is hereby corrected as shown below:

On the title page, item [54] and column 1, in the title
"RIBOFURANOSYLIMIDSZOLIUM" should read
--RIBOFURANOSYLIMIDAZOLIUM -- and "OLEATE" should read -- OLATE--

On the title page, item [75], lines 2-3, change "both of Hori" to both of Shizuoka --
item [57], line 3, change "5-oleate" to -- 5-olate --

Column 1, lines 10, 14, and 26, column 2, line 39, and column 9, claim 1, line 7, change "5-oleate" to -- 5-olate --.

This certificate supersedes Certificate of Correction issued October 15, 1996 and November 20, 1996.

Signed and Sealed this

Twenty-third Day of September, 1997

Attest:

BRUCE LEHMAN

Attesting Officer

Commissioner of Patents and Trademarks